US007981867B2

(12) United States Patent
Sim

(10) Patent No.: US 7,981,867 B2
(45) Date of Patent: Jul. 19, 2011

(54) USE OF DES-ASPARTATE-ANGIOTENSIN I
(75) Inventor: Meng Kwoon Sim, Singapore (SG)
(73) Assignee: National University of Singapore, Singapore (SG)
( * ) Notice: Subject to any disclaimer, the term of this patent is extended or adjusted under 35 U.S.C. 154(b) by 591 days.
(21) Appl. No.: 12/066,200
(22) PCT Filed: Sep. 8, 2006
(86) PCT No.: PCT/SG2006/000264
§ 371 (c)(1),
(2), (4) Date: Mar. 7, 2008
(87) PCT Pub. No.: WO2007/030082
PCT Pub. Date: Mar. 15, 2007

(65) Prior Publication Data
US 2008/0249015 A1    Oct. 9, 2008

Related U.S. Application Data
(60) Provisional application No. 60/715,156, filed on Sep. 9, 2005.

(51) Int. Cl.
*A61K 38/04* (2006.01)
*A61K 38/08* (2006.01)
*A61P 3/08* (2006.01)
(52) U.S. Cl. .................................. 514/21.6; 514/1.1
(58) Field of Classification Search .................. None
See application file for complete search history.

(56) References Cited

U.S. PATENT DOCUMENTS

| 5,773,415 A | 6/1998 | Sim |
| 5,773,416 A | 6/1998 | Chehab |
| 6,100,237 A | 8/2000 | Sim |
| 6,589,938 B2 | 7/2003 | Sim |
| 2003/0086920 A1 | 5/2003 | Sim et al. |

FOREIGN PATENT DOCUMENTS

| WO | WO 01/48247 | 7/2001 |
| WO | WO 02/10438 | 2/2002 |
| WO | WO 2004/050918 | 6/2004 |
| WO | WO 2006/003721 | 1/2006 |
| WO | WO 2007/030082 A1 | 3/2007 |

OTHER PUBLICATIONS

Definition of derivative and analog from http://cancerweb.ncl.ac.uk/omd/about.html, pp. 1-5. Accessed Jul. 7, 2005.*
Diabetes Mellitus from Merck manual, pp. 1-19. Accessed Nov. 11, 2010.*
Obesity from Merck manual, pp. 1-8. Accesssed Nov. 11, 2010.*
Bulimia Nervosa from Merck manual, pp. 1-2. Accesssed Nov. 11, 2010.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*

Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Diamond J. "The double puzzle of diabetes", 2003, 423: 599-602, Nature.
Dombrowski et al. "A new procedure for the isolation of plasma membranes, T tubules, and internal membranes from skeletal muscle", 1996, 270:E667-E676, Am J Physiol.
Fendrick et al. "The economic burden of non-influenza-related viral respiratory tract infection in the United States", 2003, 163:487-494, Arch Intern Med.
Levitt N.S. et al. "The prevalence and identification of risk factors for NIDDM in urban Africans in Cape Town, South Africa", 1993, 16:601-607, Diabetes Care.
Johasson et al. "Infection-permissive immunization with influenza virus neuraminidase prevents weight loss in infected mice", 1993, 11:1037-1039, Vaccine.
Sim M.K. et al. "Degradation of angiotensin I in the endothelium and smooth muscle of the rat aorta", 1994(a), 45:1524-1527, Biochem Pharmacol.
Sim M.K. et al. "Degradation of angiotensin I to [des-Asp1]angiotensin I by a novel aminopeptidase in the rat hypothalamus", 1994(b), 48:1043-1046, Biochem Pharmacol.
Sim M.K. and Qui X.S. "Angiotensins in plasma of hypertensive rats and human", 2003, 111:179-182, Regul Peptides.
Sullivan K.M., et al. "Estimates of the US health impact of influenza", 1993, 83:1712-1716, Am J Public Health. Dharmani et al., "Effect of des-aspartate-angiotensin I on the actions of angiotensin II in the isolated renal and mesenteric vasculature of hypertensive and STZ-induced diabetic rats," Regulatory Peptides 129:213-219 (2005).
Kuba et al., "Angiotensin-converting enzyme 2 in lung diseases," Curr. Opin. Pharmacol. 6:271-276 (2006).
Min et al., "Effects of des-aspartate-angiotensin I on angiotensin II-induced incorporation of phenylalanine and thymidine in cultured rat cardiomyocytes and aortic smooth muscle cells," Regulatory Peptides 95:93-97 (2000).
Sim and Yuan, "Effects of des-Asp-angiotensin I on the contractile action of angiotensin II and angiotensin III," Eur. J. Pharmacol 278:175-178 (1995).
Summers, "International Search Report," 7 pages, from PCT/SG2006/000264, Australian Patent Office, Woden, Australia (mailed Dec. 8, 2006).
Summers, "Written Opinion of the International Searching Authority," 7 pages, from PCT/SG2006/000264, Australian Patent Office, Woden, Australia (mailed Dec. 8, 2006).
Tochon-Danguy, "International Preliminary Report on Patentability," 17 pages, from PCT/SG2006/000264, Australian Patent Office, Woden, Australia (mailed Dec. 14, 2007).
Tochon-Danguy, "Written Opinion of the International Preliminary Examining Authority," 7 pages, from PCT/SG2006/000264, Australian Patent Office, Woden, Australia (mailed Aug. 27, 2007).

* cited by examiner

*Primary Examiner* — Julie Ha
(74) *Attorney, Agent, or Firm* — Cooley LLP

(57) ABSTRACT

The use of des-aspartate-angiotensin I, its derivatives and/or analogue thereof in medicine is described. In particular, a method for the treatment and/or prophylaxis of viral infections, for inducing hypoglycaemia and/or for reducing hyperglycaemia, and/or for treatment of hypoglycaemia-related conditions is described.

Figure 1:
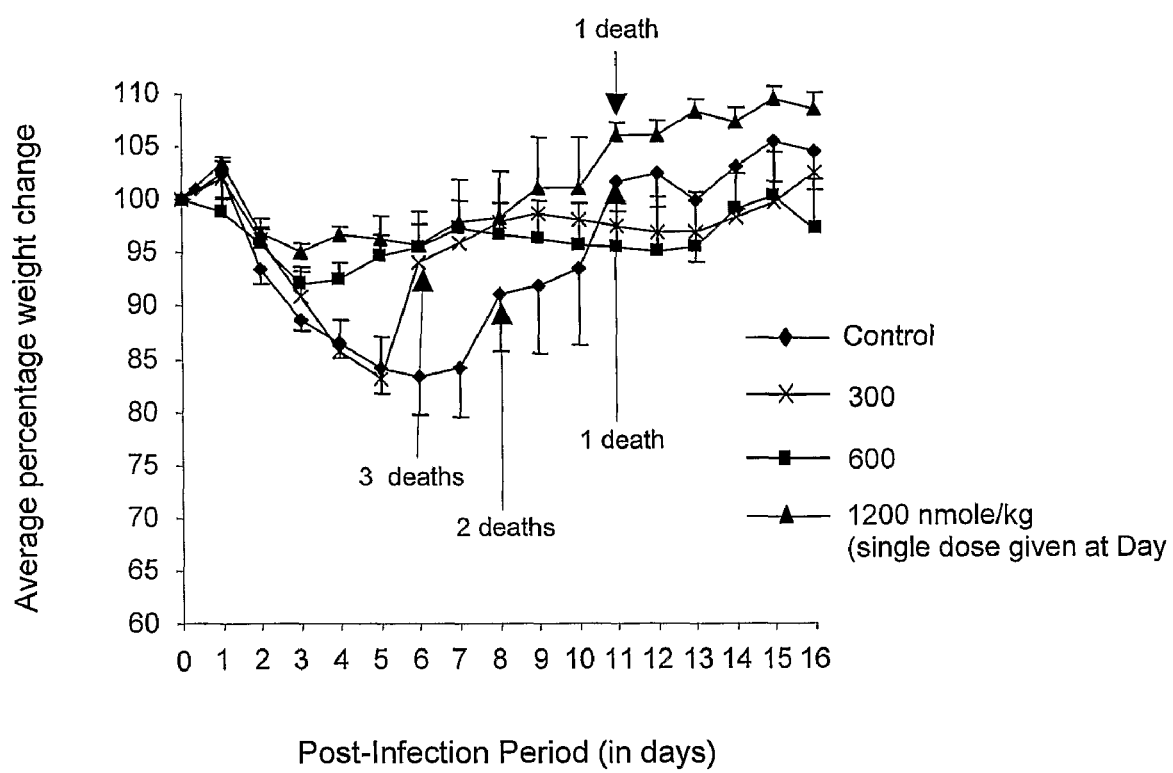

4 Claims, 6 Drawing Sheets

USE OF DES-ASPARTATE-ANGIOTENSIN I

RELATED APPLICATIONS

The present application is a U.S. National Phase Application of International Application PCT/SG2006/000264 (filed: Sep. 8, 2006) which claims the benefit of U.S. Provisional Application No. 60/715,156 (filed Sep. 9, 2005), both of which are herein incorporated by reference in their entirety for all purposes.

FIELD OF THE INVENTION

The present invention relates to the use of des-aspartate-angiotensin I (des-asp-ang I), its derivative, a functional part and/or analogue thereof in medicine.

BACKGROUND OF THE INVENTION

Viral respiratory tract infection is the most common illness in humans and the economic cost for non-influenza-related viral respiratory tract infection approaches $40 billion in the US (Fendrick A M et al., 2003), while influenza causes tens of millions of day of restricted activity, bed disability and work loss (Sullivan K M et al, 1993). There is also the ever present threat of a pandemic flu outbreak and the apparent unstoppable AIDS virus spreading far and wide. With the ability of viruses to mutate by genetic drift and genetic shift, new viruses that are not susceptible to existing vaccines will continue to come into being. There is, therefore, a need to develop more effective antiviral drugs.

Another medical condition, prolonged or chronic hyperglycemia, wherein blood glucose levels are elevated from long periods, produces many detrimental effects. This condition is exemplified by diabetes. Diabetes exacts a huge toll in money and human suffering, accounting for more than 100 billion dollars of healthcare costs annually in the United States (DiRamond J, 2003). The number of cases worldwide is estimated at 150 million with an equal number of undiagnosed cases in the First World countries and eight times more undiagnosed cases in the Third World (Levitt N S et al, 1993). The disease is characterised by high blood sugar (glucose) resulting from the defects in either insulin secretion or decreased sensitivity of the body's cells to the action of insulin, leading to a condition of hyperglycemia. Type I diabetes is currently treated by preprandial administration of exogenous insulin and dietary restriction. Current therapy of type 2 diabetes includes lifestyle modifications and the use of a variety of pharmacological agents that aim to increase insulin secretion, decrease hepatic glucose production, and/or increase insulin actions. Despite these approaches, good glycemic control is beyond the reach of most diabetic individuals, and the state of prolonged or chronic hyperglycemia can cause cardiovascular diseases, stroke, blindness, kidney failure, neurological dysfunction, necrosis and gangrene of extremities. The search for better and more specific agents with physiological properties for hyperglycemia is highly warranted.

Accordingly, any new and improved treatment of viral infections and/or conditions relating or due to hyperglycemia will be welcome.

The compound des-aspartate-angiotensin I is an endogenous angiotensin peptide (Sim M k et al, 1994, a,b). It is formed or derived from angiotensin I by a specific aminopeptidase present in blood vessels and the hypothalamus (Sim M K, Qui X S, 1994). Previous studies suggested the use of des-aspartate-angiotensin I in cardiovascular and renal actions (Sim U.S. Pat. Nos. 5,773,415, 6,100,237, 6,589,938B2 and US2003/0086920). However, no further uses are taught or suggested for des-aspartate-angiotensin I.

SUMMARY OF THE INVENTION

The present invention addresses the problems above, and in particular, provides new and effective means of treatment and/or prophylaxis of viral infections and hyperglycemia-related conditions. In particular, the present inventor has surprisingly found that at least one derivative of angiotensin I may be used in inducing hypoglycemia and/or for reducing hyperglycemia and/or for the treatment of hyperglycemia-related conditions as well as in the treatment and/or prophylaxis of viral infections. More in particular, the at least one derivative of angiotensin I is des-aspartate-angiotensin I, its derivative, a functional part, and/or an analogue thereof.

Accordingly, in one aspect, the present invention provides a method for the treatment and/or prophylaxis of at least one viral infection comprising administering to a subject des-aspartate-angiotensin I, its derivative, a functional part and/or an analogue thereof.

In another aspect, the present invention provides a method of inducing hypoglycaemia and/or reducing hyperglycaemia in a subject, the method comprising administering to the subject des-aspartate-angiotensin I, its derivative, a functional part and/or analogue thereof.

There is also provided a method of treatment and/or prophylaxis of at least one hyperglycaemia-related condition comprising administering to a subject des-aspartate-angiotensin I, its derivative, a functional part and/or analogue thereof, provided the at least one hyperglycaemia-related condition is not a renal-related disorder.

There is also provided des-aspartate-angiotensin I, its derivative, a functional part and/or analogue thereof, and/or a pharmaceutical composition thereof, for use in the treatment and/or prophylaxis of at least one viral infection.

There is also provided des-aspartate-angiotensin I, its derivative, a functional part and/or analogue thereof, and/or a pharmaceutical composition thereof, for use in the induction of hypoglycaemia and/or reduction of hyperglycaemia. There is also provided des-aspartate-angiotensin I, its derivative, a functional part and/or analogue thereof, and/or a pharmaceutical composition thereof, for use in the treatment and/or prophylaxis of at least one hyperglycaemia-related condition, provided the at least one hyperglycaemia-related condition is not a renal-related disorder.

There is also provided the use of des-aspartate-angiotensin I, its derivative, a functional part and/or analogue thereof for the preparation of a medicament for the treatment and/or prophylaxis of at least one viral infection; for the induction and/or reduction of hyperglycaemia; as well as for the treatment and/or prophylaxis of at least one hyperglycaemia-related condition, provided the at least one hyperglycaemia-related condition is not a renal-related disorder.

In another aspect, the present invention provides a kit for the treatment and/or prophylaxis of at least one viral infection comprising des-aspartate-angiotensin I, its derivative, a functional part and/or analogue thereof.

In another aspect, the present invention provides a kit for the induction of hypoglycaemia and/or reduction of hyperglycaemia comprising des-aspartate-angiotensin I, its derivative, a functional part and/or analogue thereof. There is also provided a kit for the treatment and/or prophylaxis of at least one hyperglycaemia-related condition provided the at least one hyperglycaemia-related condition is not a renal-related disorder, the kit comprising des-aspartate-angiotensin I, its derivative, a functional part and/or analogue thereof.

Under the relevant aspects above, the at least one viral infection may be a respiratory viral infection. In particular, the viral infection may be an influenza virus infection such as an influenza A infection.

The at least one hyperglycaemia-related condition may be type I diabetes, obesity, and/or bulimia nervosa.

The des-aspartate-angiotensin I, its derivative, a functional part and/or analogue thereof, may be administered in a pharmaceutically and/or therapeutically effective amount. The des-aspartate-angiotensin I, its derivative, a functional part and/or analogue thereof, may comprise at least one pharmaceutically-acceptable carrier, excipient, diluent and/or adjuvant.

The kits may further comprise information and/or instructions pertaining to their use.

BRIEF DESCRIPTION OF THE FIGURES AND TABLES

Figures:

FIG. 1 shows the effect of des-aspartate-angiotensin I on weight loss and survival of influenza A virus-infected female BALB/c mice. Six to 7 week-old mice were intranasally infected with 50 µL passage-6 lung homogenate (equivalent to 2.5×105 TCID50 of influenza A in MDCK cells). Group of 5-9 mice were then orally administered with one of the following doses of des-aspartate-angiotensin I:—300 nmole/kg/dat for 8 days (n=5), 600 nmole/kg/day for 8 days (n=9), and 120 nmole/kg administered on Day 2 post-infection (n=9, only one dose was administered). The control group (n=8) was similarly administered water for 8 days. The weight and survival of the mice were recorded daily for 16 days.

FIGS. 2 to 6 show the effect of des-aspartate-angiotensin I on blood glucose profile animal models of diabetes.

Figure 2:
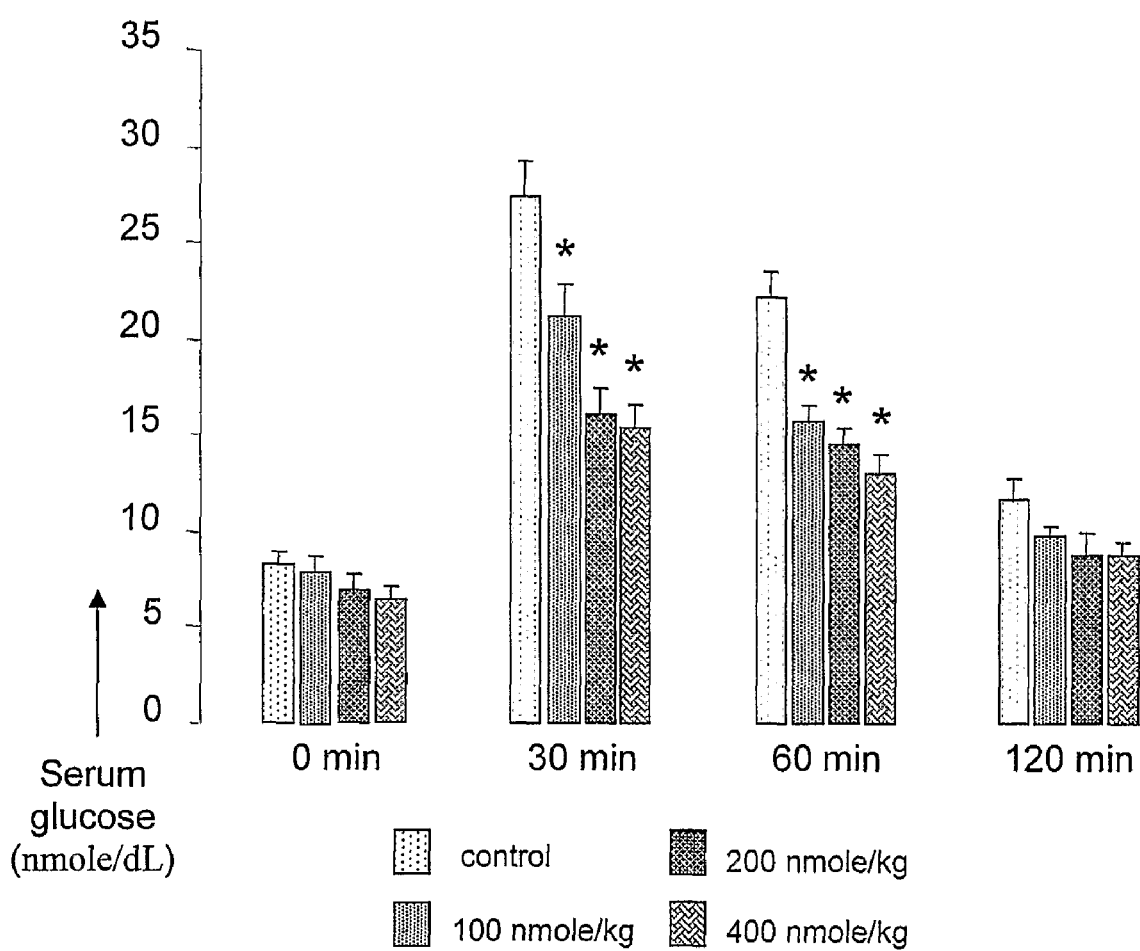

FIG. 2 shows the effect of des-aspartate-angiotensin I on blood glucose profile in diabetic KK-Ay mice. The diabteic KKAy mice were divided into four groups consisting of 6 animals per group. Animals in the control group were intraperitoneally administered 0.1 mL saline. Animals in the second, third, and fourth groups were similarly administered with 100, 200, 400 nmole/kg des-aspartate-angiotensin I, respectively. Treatment with saline and des-aspartate-angiotensin I was carried out daily for 4 weeks. Following this, animals were fasted overnight for 16 hours and oral glucose tolerance test was performed as follows: blood was withdrawn from the orbital sinus for blood glucose determination (time of withdrawal was designated as 0 time), animals were then orally administered glucose (2 g/kg), and blood was withdrawn at 30, 60 and 120 min for blood glucose determination. The blood was allowed to clot and blood glucose was measured as serum glucose using a commercial glucose kit from Thermo Electron Corporation, Australia. *Significantly different from the corresponding values of the control untreated mice ($p<0.05$, ANOVA followed by post hoc Tukey test).

Figure 3:
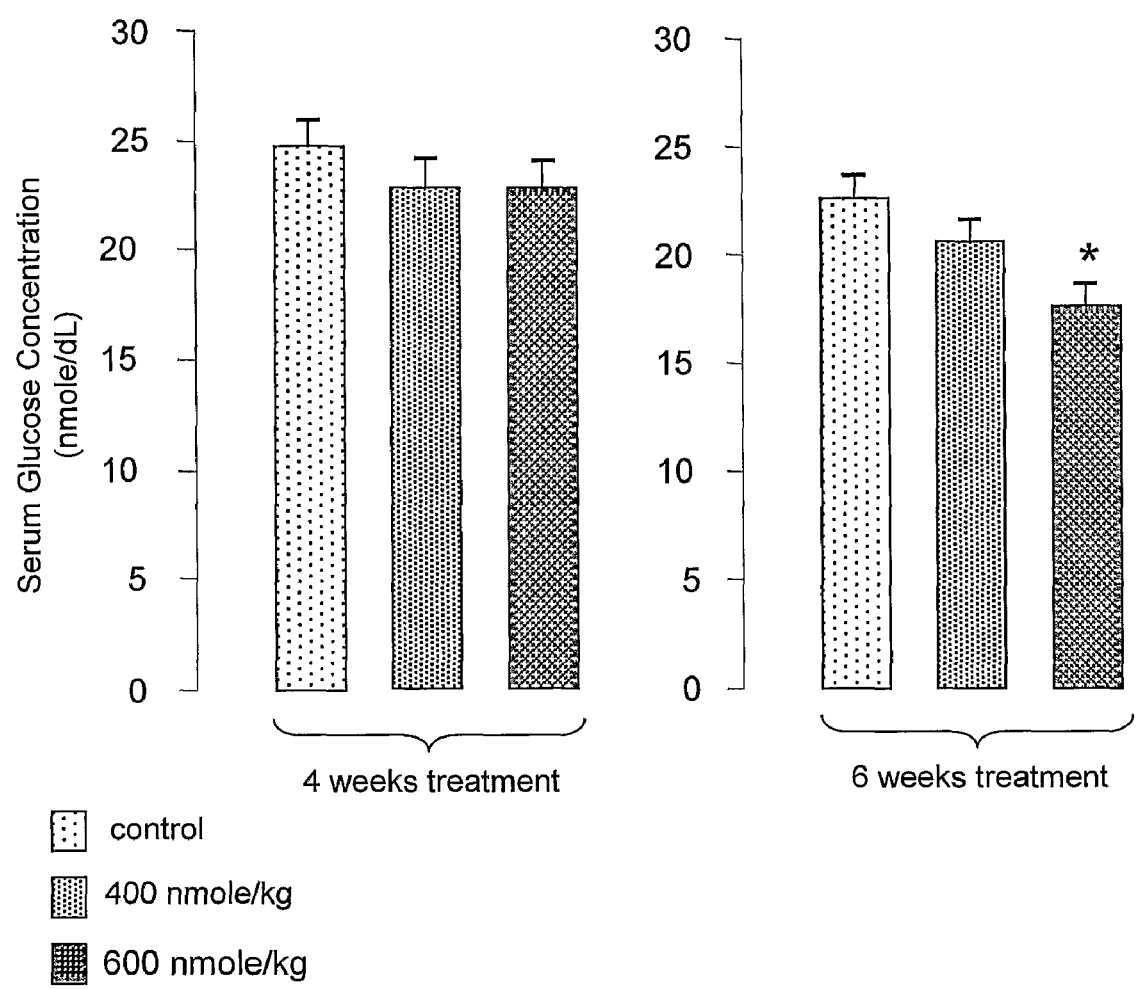

FIG. 3 shows the effect of orally administered des-aspartate-angiotensin II on blood glucose profile in diabetic GK rats at 4 and 6 weeks of treatment. The experiment was similarly carried as for KKAy mice. Control animals were administered (by gavage) 0.2 mL of water and groups 1 and 2 animals were similarly administered 400 and 600 nmole/kg des-aspartate-angiotensin I in 0.2 mL water, respectively, for a period 8 weeks. Oral glucose tolerance test (determined at 30 min) was carried out after 4 and 6 weeks of treatment. N=5 to 6. *Significantly different from the corresponding values of the control untreated rat ($p<0.05$, ANOVA followed by post hoc Tukey test). Data obtained after 8 week of treatment are given in another figure, FIG. 4. Note: The data show that orally administered DAA-1 exerts hypoglycaemic action in diabetic GK rats after 6 weeks of treatment.

Figure 4:
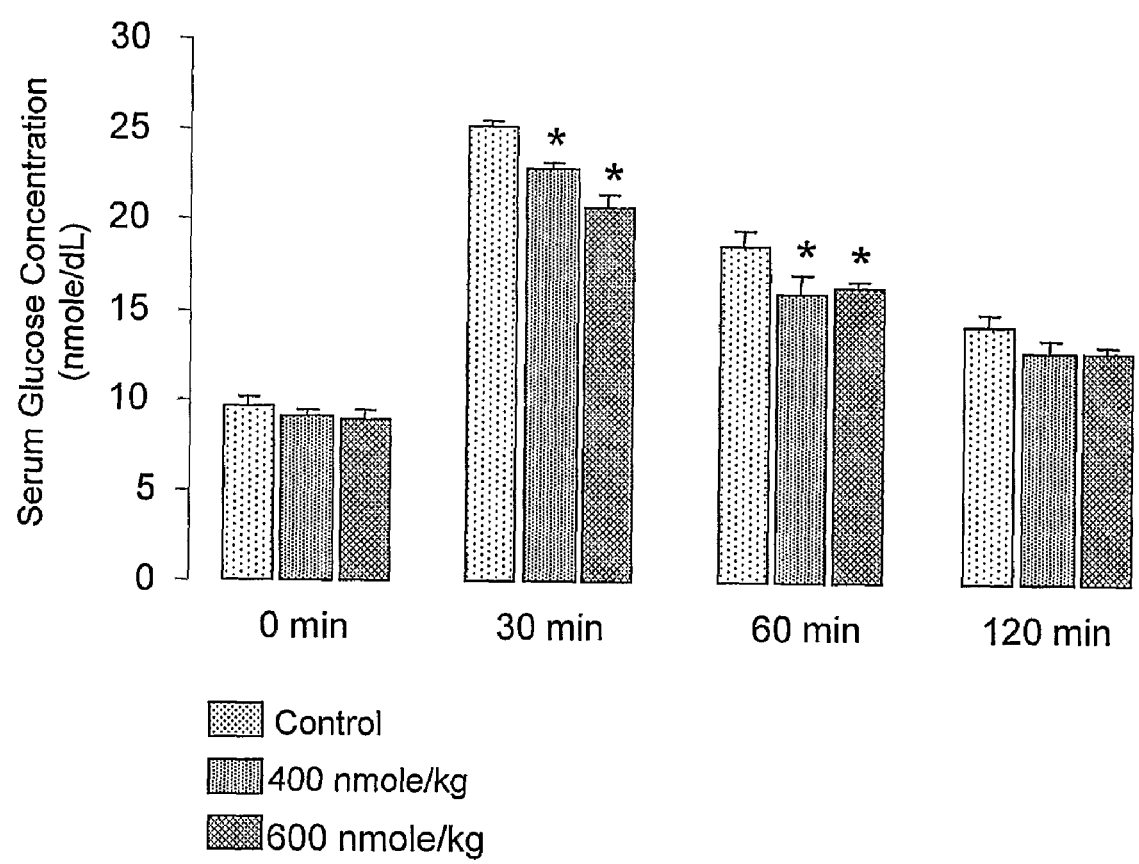

FIG. 4 shows the effect of orally administered des-aspartate-angiotensin I on blood glucose profile in diabetic GK rats at 8 weeks of treatment. This figure gives the data of a full oral glucose tolerance test conducted at 8 weeks of the same experiment described in FIG. 3. *Significantly different from the value of the corresponding control ($p<0.05$, ANOVA post hoc Tukey test).

Figure 5:
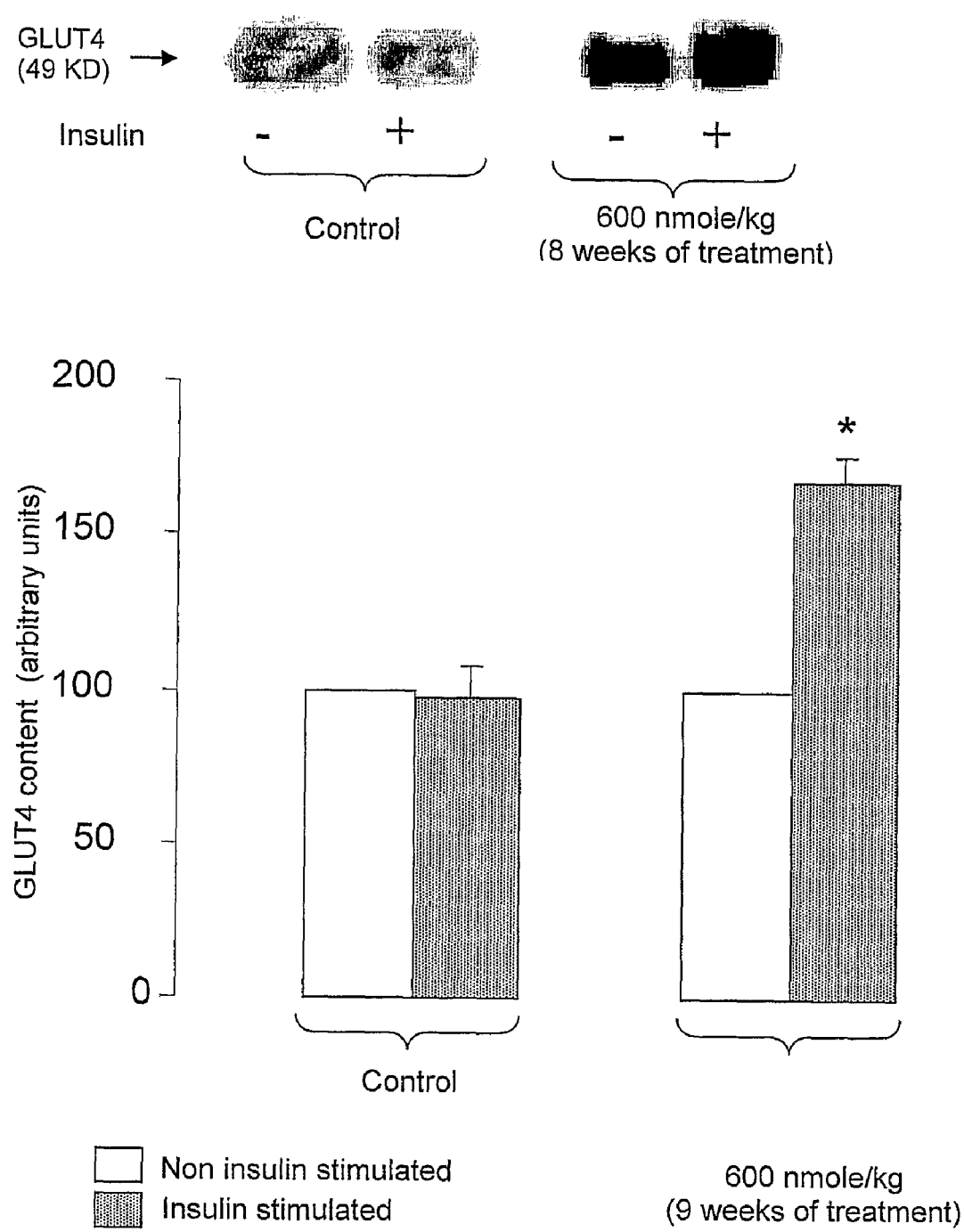

FIG. 5 shows the Effects of des-aspartate-angiotesnin I on insulin-induced translocation of GLUT-4 in skeletal muscle of diabetic GK rats. Upper panel: Representative Western blot of plasma membrane GLUT4 in skeletal muscle of des-aspartate-angiotensin I treated and non treated diabetic GK rats. Lower panel: Relative (to the non insulin stimulated samples) levels of plasma membrane GLUT4 in skeletal muscle of des-aspartate-angiotensin I treated and control diabetic GK rats. N=3 for each histogram. *Significantly different from the value of the corresponding control ($p<0.05$, ANOVA post hoc Tukey test).

Figure 6:
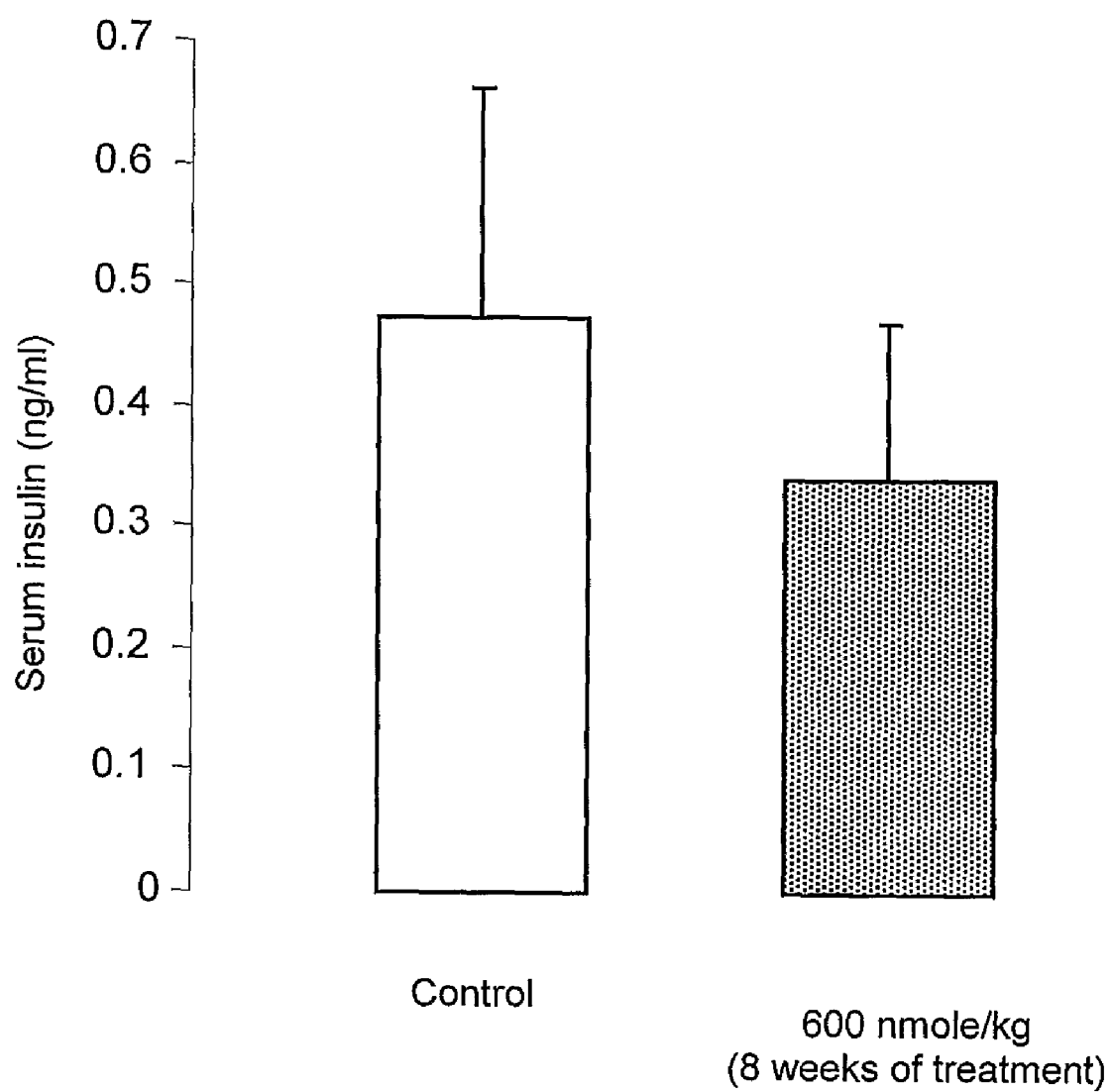

FIG. 6 shows the effect of des-aspartate-angiotesnin I on serum insulin level of diabetic GK rats. Serum from 8 weeks treated animals (as described in EXAMPLE 9) were assayed for insulin concentration by the "Ultra Senstive Rat Insulin ELISA kit" (Crystal Chem. Inc., IL, USA). The values were from serum taken at 30 min of the oral glucose tolerance test. There were no significant difference between the values of the control and treated group.

TABLES

Table 1 shows some examples of unnatural amino acids contemplated by the present invention.
Tables 2 and 3 show the effect of des-aspartate-angiotensin I in animal models of influenza.
Table 2 shows the percentage weight change and survival of influenza A virus-infected BALB/c mice treated with orally-administered des-aspartate-angiotensin I
Table 3 shows the percentage weight change and survival of influenza A virus-infected BALB/c mice treated with intraperitoneally-administered des-aspartate-angiotensin I
Tables 4 and 5 show the effects of des-aspartate-angiotensin I in control of blood glucose levels in animal models of diabetes.
Table 4 shows the data of the oral glucose tolerance test carried out in diabetic KKAy mice that were treated with intraperitoneally-administered des-aspartate-angiotensin I
Table 5 shows data of oral the glucose tolerance test carried out in diabetic KKAy mice that were treated with orally-administered des-aspartate-angiotensin I.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

Des-aspartate angiotensin I have been previously described for use in treatment of certain disorders. For example, the effect of des-aspartate angiotensin I in segmental glomerulosclerosis rat model resembling renal lesions in humans arising from various disorders including those arising from diabetus mellitus was previously determined (US2003/0086920).

However, the prior art does not teach or suggest use of des-aspartate-angiotensin I, its derivative, a functional part and/or analogue thereof for the treatment and/or prophylaxis of viral infections and/or for the induction of hypoglycaemia and/or reduction of hyperglycemia-related conditions. In particular, the present invention relates to the use of des-aspar-atate-angiotensin I in the treatment of hyperglicemia-related condition(s), excluding renal-related disorders. In particular, the condition(s) treated according to the present invention do not include renal-related disorders described in US2003/0086920.

The present invention relates to the use of des-aspartate-angiotensin I, its derivative, a functional part and/or analogue thereof for the treatment and/or prophylaxis of viral infections and/or for the induction of hypoglycaemia and/or the reduction of hyperglycaemia. In particular, the present invention relates to the use of des-aspartate-angiotensin I, its derivative, a functional part and/or analogue thereof for the treatment and/or prophylaxis of influenza A infection and hyperglycaemia-related conditions as type I diabetes, obesity, and/or bulimia nervosa.

While researching the effects of des-aspartate-angiotensin I on the cardiopulmonary functions of influenza A virus-infected mice, it was surprisingly discovered that des-aspartate-angiotensin I increased the survival of the animals.

Similarly, it was surprisingly discovered that des-aspartate-angiotensin I exerts marked hypoglycaemic effects in animal models of hyperglycaemia. Accordingly, the present invention provides new treatments, prophylaxes and/or pharmaceutical compositions for viral infections and/or hyperglycemia-related conditions using its des-aspartate-angiotensin I, its derivative, functional part, and/or analogue thereof.

Treatment of Viral Infections

The present invention provides a method for the treatment and/or prophylaxis of at least one viral infection and its symptoms comprising administering to a subject des-aspartate-angiotensin I, its derivative, a functional part and/or an analogue thereof. In particular, the des-aspartate-angiotensin I may be administered in a therapeutically and/or pharmaceutically effective amount. More in particular, the method may comprise administering to a subject an therapeutically and/or pharmaceutically effective amount of at least one derivative of angiotensin I, according to the present invention, for a time and under conditions sufficient for the onset of the viral infection and/or its symptoms to be prevented, inhibited and/or delayed or the symptoms of the viral infection to be ameliorated. The derivative may be des-aspartate-angiotensin I, or a derivative, homologue and/or analogue thereof.

The at least one viral infection may be a respiratory viral infection. In particular, the viral infection may be an influenza virus infection such as an influenza A infection.

Induction of Hypoglycaemia/Reduction of Hyperglycemia

In another aspect, the present invention also provides a method of inducing hypoglycaemia and/or reducing hyperglycemia in a subject, the method comprising administering to the subject des-aspartate-angiotensin I, its derivative, a functional part and/or analogue thereof.

In particular, the present invention provides a method of treatment and/or prophylaxis of at least one hyperglycaemia-related condition comprising administering to a subject des-aspartate-angiotensin I, its derivative, a functional part and/or analogue thereof, wherein the at least one hyperglycaemia-related condition excludes renal-related disorders.

In particular, the present invention provides a method for the treatment and/or prophylaxis of at least one of the following states or conditions: hyperglycaemia, particularly prolonged or uncontrolled hyperglycaemic conditions as in type I diabetes, obesity, bulimia nervosa excluding renal disorders arising from hyperglycaemia as in Type 2 diabetes (diabetes mellitus), the method comprising administering to a subject at least one derivative of angiotensin I. In particular, the at least one derivative of angiotensin I is des-aspartate-angiotensin I, its derivative, a functional part and/or analogue thereof. In particular, the angiotensin I derivative is administered for a time and under conditions sufficient for the condition and/or its symptoms to be prevented, inhibited, delayed and/or ameliorated.

The present invention also provides des-aspartate-angiotensin I or a pharmaceutical composition therefore for use in the treatment and/or prophylaxis of hyperglcaemia, in particular prolonged or uncontrolled hyperglycaemic conditions as in type I diabetes, obesity, bulimia nervosa excluding renal disorders arising from hyperglycemia as in Type 2 diabetes mellitus, The pharmaceutical composition may comprise at least one derivative of angiotensin I according to the present invention and, optionally, a pharmaceutically acceptable carrier, excipient, adjuvant and/or diluent.

The compositions may be administered in a therapeutically and/or pharmaceutically effective dose, and/or for a time and under conditions sufficient for its symptoms to be prevented, inhibited or delayed and/or ameliorated.

Throughout this specification, unless the context requires otherwise, the word "comprise", or variations such as "comprises" or "comprising, will be understood to imply the inclusion of a stated element or integer or group of elements or integers but not the exclusion of any other element or integer or group of elements or integers.

An "effective amount" refers to an amount effective, at dosages and for periods of time necessary to achieve the desired therapeutic result, such as to prevent, inhibit and/or delay the onset hyperglycaemia-related disorders and/or ameliorate the symptoms of hyperglycaemia-related disorders. While the effective amount may vary according to various factors such as the disease state, age, sex, and weight of the individual.

A derivative of des-aspartate-angiotensin I includes any mutant, fragment, part and/or portion of angiotensin I or des-aspartate-angiotensin I including molecules comprising single or multiple amino acid substitutions, deletions and/or additions to angiotensin I or to des-aspartate-angiotensin I. The processes of substitutions, deletions and/or additions may result in a derivative or peptide that has more amino acids than the original angiotensin I or des-aspartate-angiotensin I. The processes of substitutions, deletions and/or additions may result in a derivative or peptide that has more amino acids than the original angiotensin I or des-aspartate angiotensin I The preferred derivative in accordance with the present invention is des-aspartate-angiotensin I or a derivative, homologue and/or analogue thereof. Reference to a homologue and/or an analogue includes a mimotope or peptide and/or analogue mimetic. Such derivatives, homologues and/or analogues may function in place of des-aspartate-angiotensin I and/or its equivalent or they may act as an agonist thereof or, when necessary, an antagonist thereof.

As stated above, a derivative includes single or multiple amino acid substitutions, additions and/or deletions to des-aspartate-angiotensin I and/or angiotensin I. The final derivative is a peptide having similar functions and consists of no less than two amino acid sequence of the original angiotensin I or des-aspartate-angiotensin.

Amino acid insertional derivatives of des-Asp-angiotensin I include amino and/or carboxyl terminal fusions as well as intra-sequence insertions of single or multiple amino acids. Insertional amino acid sequence variants are those in which one or more amino acid residues are introduced into a predetermined site in the des-aspartate-angiotensin I although random insertion is also possible with suitable screening of the resulting product.

Deletional variants are characterized by the removal of one or more amino acids from the sequence. Substitutional amino acid variants are those in which at least one residue in the sequence has been removed and a different residue inserted in its place.

Where the des-aspartate-angiotensin I is derivatized by amino acid substitution, the amino acids are generally replaced by other amino acids having like properties, such as hydrophobicity, hydrophilicity, electronegativity, bulky side chains and the like. Amino acid substitutions are either of single or multiple residues. Amino acid insertions will usually be in the order of about 1-7 amino acid residues and deletions will range from about 1-7 residues. Preferably, deletions or insertions are made in adjacent pairs, i.e. a deletion of two residues or insertion of two residues.

Homologues include functionally, structurally or stereochemically similar polypeptides from, for example, other sources such as for livestock animals, laboratory test animals or primates. The similar peptides may also be homologues of des-aspartate-angiotensin I.

Analogues and mimetics include molecules which contain non-naturally occurring amino acids as well as molecules which do not contain amino acids but nevertheless behave functionally the same as the des-aspartate-angiotensin I. Analogues contemplated herein include modifications to side chains, incorporation of unnatural amino acids and/or their derivatives during peptide synthesis and the use of crosslinkers and other methods which impose conformational constraints on the peptide molecule or their analogues.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and heterobifunctional reagents which usually contain an amino reactive moiety such as N-hydroxysuccinimide and another group specific-reactive moiety.

All these types of modifications may be important to stabilize the subject des-Asp-angiotensin I. This may be important if used, for example, in the manufacture of a vaccine or therapeutic composition or in detection assays. Examples of unnatural amino acids contemplated by the present invention are presented in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-α-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |

TABLE 1-continued

| Non-conventional amino acid | Code | Non-conventional amino acid | Code |
|---|---|---|---|
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-α-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| α-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L--methylarginine | Marg | L-α-methylasparagine | Masn |
| L--methylaspartate | Masp | L-α-methyl-t-butylglycine | Mtbug |
| L--methylcysteine | Mcys | L-methylethylglycine | Metg |
| L--methylglutamine | Mgln | L-α-methylglutamate | Mglu |
| L--methylhistidine | Mhis | L-α-methylhomophenylalanine | Mhphe |
| L--methylisoleucine | Mile | N-(2-methylthioethyl)glycine | Nmet |
| L--methylleucine | Mleu | L-α-methyllysine | Mlys |
| L--methylmethionine | Mmet | L-α-methylnorleucine | Mnle |
| L--methylnorvaline | Mnva | L-α-methylornithine | Morn |
| L--methylphenylalanine | Mphe | L-α-methylproline | Mpro |
| L--methylserine | Mser | L-α-methylthreonine | Mthr |
| L--methyltryptophan | Mtrp | L-α-methyltyrosine | Mtyr |
| L--methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Having now generally described the invention, the same will be more readily understood through reference to the following examples which are provided by way of illustration, and are not intended to be limiting to the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Source of Materials

Des-aspartate-angiotensin was purchased from Bachem (Dubendorf, Switzerland). Des-aspartate-angiotensin I can be prepared by techniques well known in the art. Influenza A/Aichi/2/68 virus and Madin-Darby Canine Kidney cells were purchased from ATCC. The virus has a titer of 106.75 CEID50/0.2 ml in 2 days on II day old SPF CE. Six to 7 weeks old female BALB/c mice were obtained from the Animal Center, National University of Singapore. Six to 7 weeks old diabetic KKAy mice were purchased from CLEA, Japan.

Example 2

Development of a Mouse Model for Influenza A Virus

Two BALB/c mice were intranasally infected with 50 μL of influenza A virus. Two days later, the infected mice were sacrificed by cervical dislocation and their lungs were removed. 0.3 g of lung tissue was homogenized in 1 mL of PBS containing 1000 units/L penicillin and 10 μg/L streptomycin. The lung homogenate was cleared of connective tissue by centrifuging at 5,000 rpm for 5 minutes on a bench-top centrifuge. This homogenate was labeled as passage-1 lung homogenate. A second batch of 2 BALB/c mice was infected with 50 μL of passage-1 lung homogenate. The process of passaging was repeated and the virus virulence and titer in each passage of lung homogenate was monitored by assaying its infectivity in Madin-Darby Canine Kidney (MDCK) cells, which is a host cell for influenza A virus. The virulence and titer of the influenza A virus increased progressively with each passage. Fifty μL of passage-6 lung homogenate, equivalent to 2.5×105 TCID50 of the virus in MDCK cells, were then used to infect 6-7 weeks old female BALB/c mice for the study of the antiviral action of des-aspartate-angiotensin I.

Example 3

Monitoring and Treatment (with Orally-Administered Des-aspartate-angiotensin I) of Influenza A Virus-Infected BALB/c Mice BALB/c mice when infected with passage-6 lung homogenate lost weight and suffered fatality. The following protocol described by Johasson et al was used to study the effect of des-aspartate-angiotensin on these parameters. Six to 7 weeks old female BALB/c mice were intranasally infected with 50 μL passage-6 lung homogenate. Groups of 5-9 mice were orally administered with one of the following dose of des-aspartate-angiotensin I:—300 nmole/kg daily for 8 days, 600 nmole/kg daily for 8 days, and 1200 nmole/kg on day 2 post virus infection (i.e. only one dose was administered). A group of 8 mice were similarly administered water for 8 days and served as the control group. The weight and survival of the mice were recorded daily for 16 days.

Example 4

Effect of Orally-Administered Des-aspartate-angiotensin I on Virus-Infected BALB/c Mice The results of the study are summarized in Table 2 and depicted in FIG. 1. The daily weight of each surviving animal was expressed as a percentage of its weight at Day 0 (i.e. day of virus inoculation). The data of the control and each treatment group were expressed as the mean I SEM. Significant differences were determined by one way ANOVA and post hoc Tukey test. The accepted level of significance was $p<0.05$. Des-aspartate-angiotensin I is an antiviral agent in term of its ability to attenuate the weight loss and survival of the virus-infected animals. Effective antiviral activity was observed with a dose of 600 nmole/kg administered daily for 8 days, and a single dose of 1200 nmole/kg given on Day 2.

Example 5

Monitoring and Treatment (with Intraperitoneally-administered Des-aspartate-angiotensin I) of Influenza A Virus-infected BALB/c Mice Thirty BALB/c mice were infected with 55 μL passage-6 lung homogenate and the weight of each animal was monitored daily as described in EXAMPLES 3 and 4. Animals were intraperitoneally administered with either 60 nmole/kg des-aspartate-angiotensin I in 0.1 ml of phosphate buffer saline (PBS) or 0.1 ml PBS on the day when their weight loss was 15% or greater during the first post-infection week. This treatment was continued for 7 days. Of the 30 animals, 14 animals lost more than 15% of their weight during the first post-infection week. Hence, 7 animals were randomly chosen for des-aspartate-angiotensin I treatment and 7 animals for vehicle treatment. The weight of the treated animals were monitored till either the animal died or regained 100% of their initial weight. Surviving animals were euthanized and their lung homogenate was prepared and assayed for influenza A virus as described in Example 2.

TABLE 2

| Post Infection | Average Percentage Weight Change (weight of individual animals at Day 0 was taken as 100%) | | | |
|---|---|---|---|---|
| Period (in Days) | Control (n = 8) | 300 nmole/kg/ day for 16 days (n = 5) | 600 nmole/kg/ day for 16 days (n = 9) | 1200 nmole/kg given as a single dose on Day 2 (n = 9) |
| 0 | 100 | 100 | 100 | 100 |
| 1 | 102.4 ± 2.2 | 102.1 ± 1.5 | 98.7 ± 1.3 | 103.5 ± 0.5 |
| 2 | 93.4 ± 1.4 | 96.2 ± 2.0 | 95.8 ± 1.4 | 96.8 ± 0.6 |
| 3 | 88.7 ± 1.0 | 90.8 ± 2.4 | 92.0 ± 1.7 | 95.1 ± 0.8* |
| 4 | 86.4 ± 1.3 | 85.8 ± 2.9 | 92.4 ± 1.8* | 96.7 ± 1.2* |
| 5 | 84.1 ± 2.3 | 83.2 ± 3.4 | 94.8 ± 1.8* | 96.3 ± 2.1* |
| 6 | 83.3 ± 3.6 | 94.1# (3) | 95.5 ± 2.1* | 95.7 ± 3.1* |
| 7 | 84.1 ± 4.6 | 95.7# | 97.8 ± 2.6* | 97.8 ± 4.0* |
| 8 | 91.0 ± 5.4 (2) | 97.9# | 96.7 ± 2.9 | 98.3 ± 4.3 |
| 9 | 91.8 ± 6.2 | 98.7# | 96.3 ± 3.5 | 101.1 ± 4.7 |
| 10 | 93.4 ± 7.1 | 98.1# | 95.6 ± 4.0 | 101.1 ± 4.8 |
| 11 | 101.6 ± 2.8 (1) | 97.4# | 95.4 ± 4.5 | 105.9 ± 1.3 (1) |
| 12 | 102.4 ± 3.1 | 96.9# | 95.1 ± 5.0 | 106.1 ± 1.3 |
| 13 | 99.9 ± 5.8 | 96.8# | 95.5 ± 5.2 | 108.1 ± 1.2 |
| 14 | 103.0 ± 3.9 | 98.2# | 99.1 ± 3.4 | 107.2 ± 1.3 |
| 15 | 105.4 ± 3.8 | 99.6# | 100.3 ± 4.2 | 109.4 ± 1.2 |
| 16 | 104.4 ± 3.5 | 102.4# | 97.0 ± 4.8 | 108.4 ± 1.5 |

*Significantly different from the corresponding control value ($p < 0.05$, ANOVA post hoc Tukey test) Bold numbers within brackets indicate number of animals that died on the day of recording.
Average value from two surviving mice i.e. no SEM.

Example 6

Effect of Intraperitoneally-administered Des-aspartate-angiotensin I on Virus-infected BALB/c Mice The data of the study are summarized in Table 3. The weight of each animal was expressed as a percentage of its weight at Day 0. All mice that were treated with saline died within a week. In the des-aspartate-angiotensin I treated mice, only I mouse died. Six animals survived and regained their original weight. No influenza A virus was detected in the lung homogenate of the surviving mice. The results show that des-aspartate-angiotensin I exerts effective antiviral action in preventing influenza A virus-infected mice from dying.

Example 7

Effect of Intraperitoneally-Administered Des-aspartate-angiotensin I on Blood Glucose Profile in Diabetic KKAy Mice The diabetic KKAy mice were divided into four groups consisting of 6 animals per group. Animals in the control group were intraperitoneally administered 0.1 mL saline. Animals in the second, third, and fourth groups were similarly administered with 100, 200, 400 nmole/kg des-aspartate-angiotensin I, respectively in 0.1 ml of PBS. Treatment with saline and des-aspartate-angiotensin I was carried out daily for 4 weeks. Following this, animals were fasted overnight for 16 hours and oral glucose tolerance test was performed as follows: blood was withdrawn from the orbital sinus for blood glucose determination (time of withdrawal was designated as 0 time), animals were then orally administered glucose (2 g/kg), and blood was withdrawn at 30, 60 and 120 min for blood glucose determination. The blood was allowed to clot and blood glucose was measured as serum glucose using a commercial glucose kit from Thermo Electron Corporation, Australia. Table 3 shows that des-aspartate-angiotensin I, administered at doses of 200 and 400 nmole/kg/day for 4 weeks, significantly lowered the blood glucose level at 30 and 60 min of the oral glucose tolerance test. The data, graphically displayed in FIG. 2, show that des-aspartate-angiotensin I possesses hypoglycaemic action and can be use to treat the symptoms of hyperglycaemia.

Example 8

Dose-Range Finder Experiment for Orally Administered Des-aspartate-angiotensin I A dose-range finder experiment to determine the hypoglycaemic dose for orally administered des-aspartate-angiotensin I was also carried out. In this experiment, the animals in each of the three treatment groups of 7 diabetic KKAy mice were orally administered (by gavage) 200, 400, and 600 nmole/kg/day des-aspartate-angiotensin I in volume of 0.1 mL, respectively. Animals in the control group were similarly administered 0.1 mL water. The treatment period was 4 weeks. Oral glucose tolerance test was carried out as described in Example 5, except that blood was sampled at 0 and 30 min. The data, presented in Table 4, show that des-aspartate-angiotensin I is an effective oral hyperglycemic agent at an oral dose of 600 nmole/kg.

Example 9

Effect of Orally-Administered Des-aspartate-angiotensin I on Blood Glucose Profile in Diabetic KKAy Mice In this experiment, the animals in each of the three treatment groups of 7 diabetic KKAy mice were orally administered (by gavage) 200, 400, and 600 nmole/kg/day des-aspartate-angiotensin I in volume of 0.1 mL water, respectively. Animals in the control group were similarly administered 0.1 mL water. The treatment period was 4 weeks. Oral glucose tolerance test was carried out as described in EXAMPLE 7, except that blood was sampled at 0 and 30 min. The data, presented in Table 5, show that des-aspartate-angiotensin I exerts significant hypoglycaemic action at an oral dose of 600 nmole/kg.

Example 10

Effect of Orally-administered Des-aspartate-angiotensin I on Blood Glucose Profile in Diabetic GK Rats Diabetic GK rats were divided into three groups, consisting of six animals in each group. Animals in groups 1 and 2 were administered, by gavage, one of the following: 400 or 600 nmole/kg of des-aspartate-angiotensin I in a volume of 0.2 mL water daily for up to 8 weeks. Control animals in group 3 were similarly administered 0.2 mL water. Thirty min oral glucose tolerance test was performed fortnightly as a spot test to detect significant hypoglycaemic action (if any) that arose from des-aspartate-angiotensin I treatment. As shown in FIG. 3, significant hypoglycaemic action was detected at 6 weeks of treatment. Animals were treated for a further 2 weeks and a full oral glucose tolerance test was performed thereafter. The data, presented in FIG. 4, show that the hypoglycaemic action of des-aspartate-angiotensin I was also significantly expressed at 8 weeks of treatment. The results of this study show that des-aspartate-angiotensin I is an effective oral hypoglycaemic agent and can be used to treat the hyperglycemia in diabetes.

Example 11

Effect of Orally-Administered Des-aspartate-angiotensin I on Insulin-induced Translocation of Glucose Transporter-4 (GLU4) to Plasma Membrane in Skeletal Muscles of Diabetic GK Rats The diabetic GK rats described in EXAMPLE 9 were similarly treated for another week. At 9 weeks of treatment, animals were fasted overnight and half the animals in each group were intraperitoneally administered with PBS and the other half with insulin (0.5 U/kg). After 30 minutes, the animals were sacrificed by cervical dislocation. Hind limb skeletal muscles were rapidly excised and frozen in liquid nitrogen. Muscle samples were stored at −80° C. until used. The hindlimb muscles were subsequently thawed over an ice pack and plasma membranes were prepared as described by Dombrowaski et al. Thirty μg of protein from the 25% interface of the discontinued sucrose gradient was subjected to SDS-PAGE, transferred to PVDF sheets and incubated with anti-GLUT4 polyclonal primary antibody (1:800), washed and followed by incubation with anti-goat secondary antibody (1:10,000). The bands were detected at 49 kDa. The data, presented in FIG. 5, show that des-aspartate-angiotensin I significantly enhances the insulin-induced translocation of GLUT4 to the plasma membrane in skeletal muscle of diabetic GK rats. As insulin resistance is the hallmark of diabetes, it is concluded that the des-aspartate-angiotensin I exerts marked hypoglycaemic action in diabetic GK rats by overcoming insulin resistance in these animals. This is especially so as serum level of insulin was not significantly affected in the same diabetic GK rats that were treated with 600 nmole/kg of des-aspartate-angiotensin I (see FIG. 6 for details).

Example 12

Kit

The present invention provides a kit comprising des-aspartate-angiotensin I, its derivative, a functional part and/or an analogue thereof for the treatment and/or prophylaxis of at least one viral infection and/or for the induction of hypoglycaemia and/or reduction of hyperglycaemia. There is also provided a kit for the treatment and/or prophylaxis of a hyperglycaemia-related condition excluding renal-related disorders. The kit may further comprise information and/or instruction pertaining to its use.

TABLE 3

Percentage Weight Change of Individual Mouse

| Post Infection Period | Saline treated mice | | | | | | | Des-aspartate-angiotensin I treated mice | | | | | | |
|---|---|---|---|---|---|---|---|---|---|---|---|---|---|---|
| (in Days) | 1 | 2 | 3 | 4 | 5 | 6 | 7 | 1 | 2 | 3 | 4 | 5 | 6 | 7 |
| 0 | 100.0 | 100.0 | 100.0 | 100.0 | 100.0 | 100.0 | 100.0 | 100.0 | 100.0 | 100.0 | 100.0 | 100.0 | 100.0 | 100.0 |
| 1 | 99.4 | 98.1 | 98.7 | 99.2 | 99.5 | 99.3 | 94.8 | 99.4 | 100.4 | 99.0 | 98.4 | 99.3 | 98.5 | 98.9 |
| 2 | 96.5 | 97.1 | 97.5 | 97.9 | 98.2 | 96.6 | 87.8 | 99.3 | 99.8 | 96.3 | 97.1 | 96.6 | 97.3 | 95.8 |
| 3 | 89.8 | 96.8 | 96.4 | 96.8 | 95.8 | 93.9 | 86.0 | 99.4 | 99.0 | 90.3 | 94.6 | 88.6 | 94.7 | 93.9 |
| 4 | 88.2 | 93.2 | 93.1 | 86.0 | 85.7 | 87.5 | 81.5 | 97.5 | 96.6 | 85.7 | 86.2 | 83.3 | 92.1 | 90.8 |
| 5 | 87.7 | 86.5 | 90.9 | 80.7 | 82.0 | 84.7 | 80.1 | 90.3 | 91.7 | 82.8 | 85.7 | 81.0 | 90.1 | 89.0 |
| 6 | 81.8 | 82.9 | 86.7 | 76.8 | 78.7 | 83.4 | 78.6 | 87.5 | 87.4 | 80.8 | 82.7 | 78.2 | 85.2 | 88.8 |
| 7 | 80.9 | 81.1 | 84.1 | 69.8 | 77.4 | 78.4 | 73.9 | 85.0 | 83.8 | 80.7 | 76.8 | 73.9 | 82.8 | 84.4 |
| 8 | 74.6 | 79.4 | 81.5 | 65.4 | 74.9 | 76.3 | 69.4 | 86.2 | 80.4 | 79.7 | 72.9 | 71.2 | 83.2 | 82.4 |
| 9 | 71.8 | 75.3 | 80.1 | died | 72.7 | 74.0 | 65.1 | 90.3 | 78.8 | 81.4 | 69.9 | 71.8 | 80.5 | 78.6 |
| 10 | 70.8 | 70.6 | 76.4 | | 69.4 | 71.0 | 61.0 | 93.0 | 77.5 | 80.5 | 69.0 | 73.2 | 82.3 | 77.7 |
| 11 | 69.6 | died | 72.6 | | 68.2 | 68.9 | died | 99.3 | 77.1 | 82.1 | 67.7 | 75.8 | 88.9 | 74.5 |
| 12 | 68.8 | | died | | died | died | | 101.2 | 78.9 | 80.0 | 64.9 | 80.1 | 88.9 | 74.5 |
| 13 | died | | | | | | | | 80.8 | 76.6 | 63.0 | 82.8 | 97.4 | 72.3 |
| 14 | | | | | | | | | 82.6 | 75.2 | 61.3 | 86.3 | 102.8 | 74.0 |
| 15 | | | | | | | | | 84.3 | 83.0 | 58.9 | 90.1 | | 76.7 |
| 16 | | | | | | | | | 89.4 | 90.3 | 58.9 | 94.6 | | 78.6 |
| 17 | | | | | | | | | 94.8 | 93.5 | 58.7 | 99.3 | | 81.2 |
| 18 | | | | | | | | | 98.7 | 99.1 | died | 101.0 | | 83.2 |
| 19 | | | | | | | | | 100.9 | 100.8 | | | | 86.8 |
| 20 | | | | | | | | | | | | | | 91.8 |
| 21 | | | | | | | | | | | | | | 95.7 |
| 22 | | | | | | | | | | | | | | 98.4 |
| 23 | | | | | | | | | | | | | | 100.1 |

TABLE 4

| Dose of des-aspartate-angiotensin I | Serum glucose level at different sampling time (nmole/dL) | | | |
|---|---|---|---|---|
| | 0 min | 30 min | 60 min | 120 min |
| Control | 8.3 ± 0.6 | 27.3 ± 1.9 | 22.2 ± 1.3 | 12.2 ± 1.3 |
| 100 nmole/kg | 7.9 ± 0.9 | 21.2 ± 1.6* | 13.4 ± 1.3* | 9.9 ± 0.5 |
| 200 nmole/kg | 6.9 ± 0.9 | 16.0 ± 1.4* | 14.5 ± 0.9* | 8.7 ± 1.2 |
| 400 nmole/kg | 6.5 ± 0.6 | 15.4 ± 1.6* | 13.0 ± 1.1* | 8.8 ± 0.6 |

*Significantly different from the corresponding value of the Control ($p < 0.05$, ANOVA post hoc Tukey test)

TABLE 5

| Dose of des-aspartate-angiotensin I | Serum glucose level at different sampling time (nmole/dL) | |
|---|---|---|
| | 0 min | 30 min |
| Control | 9.0 ± 1.0 | 33.7 ± 1.7 |
| 200 nmole/kg | 8.9 ± 1.0 | 37.7 ± 2.6 |
| 400 nmole/kg | 9.1 ± 1.6 | 26.0 ± 3.6 |
| 600 nmole/kg | 8.9 ± 0.7 | 17.5 ± 1.9* |

*Significantly different from the corresponding value of the Control ($p < 0.05$, ANOVA post hoc Tukey test)

REFERENCES

DiRamond J. The double puzzle of diabetes. Nature 2003; 423: 599-602.

Dombrowski et al A new procedure for the isolation of plasma membranes, T tubules, and internal membranes from skeletal muscle. Am J Physiol 1996; 270:E667-E676.

Fendrick et al. The economic burden of non-influenza-related viral respiratory tract infection in the United States. Arch Intern Med 2003; 163:487-494.

Levitt N S et al., The prevalence and identification of risk factors for NIDDM in urban Africans in Cape Town, South Africa. Diabetes Care 1993; 16:601-607.

Johasson et al., Infection-permissive immunization with influenza virus neuraminidase prevents weight loss in infected mice. Vaccine 1993; 11:1037-1039.

Sim M K et al. Degradation of angiotensin I in the endothelium and smooth muscle of the rat aorta. Biochem Pharmacol 1994(a); 45:1524-1527.

Sim M K et al., Degradation of angiotensin I to [des-Asp1] angiotensin I by a novel aminopeptidase in the rat hypothalamus. Biochem Pharmacol 1994(b); 48:1043-1046.

Sim M K, Qui X S. Angiotensins in plasma of hypertensive rats and human. Regul Peptides 2003; 111:179-182.

Sullivan K M, et al. Estimates of the US health impact of influenza. Am J Public Health 1993; 83:1712-1716.
U.S. Pat. No. 5,773,416
U.S. Pat. No. 6,100,237
U.S. Pat. No. 6,589,938 B2
US 2003/0086920

The invention claimed is:

1. A method of treatment of at least one hyperglycaemia-related condition comprising administering to a subject in need thereof des-aspartate-angiotensin I, wherein the hyperglycaemia-related condition is not a renal-related disorder.

2. The method according to claim 1, wherein the hyperglycaemia-related condition is type I diabetes, obesity, and/or bulimia nervosa.

3. The method according to claim 1, wherein the des-aspartate-angiotensin I, is administered in a effective amount.

4. The method according to claim 1, wherein the des-aspartate-angiotensin I, is administered in combination with at least one pharmaceutically-acceptable carrier, excipient, diluent and/or adjuvant.

* * * * *

UNITED STATES PATENT AND TRADEMARK OFFICE
CERTIFICATE OF CORRECTION

PATENT NO. : 7,981,867 B2  Page 1 of 1
APPLICATION NO. : 12/066200
DATED : July 19, 2011
INVENTOR(S) : Meng Kwoon Sim It is certified that error appears in the above-identified patent and that said Letters Patent is hereby corrected as shown below:

In the claims at column 18, lines 1-4, claim 2 should appear as follows:

2. The method according to claim 1, wherein the hyperglycaemia-related condition is type I diabetes, --type II diabetes,-- obesity, and/or bulimia nervosa.

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 7,981,867 B2 | Page 1 of 1 |
| APPLICATION NO. | : 12/066200 | |
| DATED | : July 19, 2011 | |
| INVENTOR(S) | : Meng Kwoon Sim | |

It is certified that error appears in the above-identified patent and that said Letters Patent is hereby corrected as shown below:

In the claims at column 18, lines 1-3, claim 2 should appear as follows:

2. The method according to claim 1, wherein the hyperglycaemia-related condition is type I diabetes, --type II diabetes,-- obesity, and/or bulimia nervosa.

This certificate supersedes the Certificate of Correction issued May 6, 2014.

Signed and Sealed this
Third Day of June, 2014

Michelle K. Lee
*Deputy Director of the United States Patent and Trademark Office*